United States Patent
Huang et al.

(10) Patent No.: US 9,918,627 B2
(45) Date of Patent: Mar. 20, 2018

(54) AQUEOUS CELL DIFFERENTIATION IN ANTERIOR UVEITIS USING OPTICAL COHERENCE TOMOGRAPHY

(71) Applicants: David Huang, Portland, OR (US); Yan Li, Portland, OR (US); James T. Rosenbaum, Portland, OR (US); Jennifer Rose-Nussbaumer, San Francisco, CA (US)

(72) Inventors: David Huang, Portland, OR (US); Yan Li, Portland, OR (US); James T. Rosenbaum, Portland, OR (US); Jennifer Rose-Nussbaumer, San Francisco, CA (US)

(*) Notice: Subject to any disclaimer, the term of this patent is extended or adjusted under 35 U.S.C. 154(b) by 197 days.

(21) Appl. No.: 14/704,175

(22) Filed: May 5, 2015

(65) Prior Publication Data

US 2015/0324978 A1    Nov. 12, 2015

Related U.S. Application Data

(60) Provisional application No. 61/989,196, filed on May 6, 2014.

(51) Int. Cl.
| | |
|---|---|
| *G06K 9/00* | (2006.01) |
| *A61B 3/10* | (2006.01) |
| *G06T 7/00* | (2017.01) |
| *A61B 3/117* | (2006.01) |

(52) U.S. Cl.
CPC .............. *A61B 3/102* (2013.01); *A61B 3/117* (2013.01); *G06T 7/0012* (2013.01); *G06T 2207/10101* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 6,325,512 B1 | 12/2001 | Wei | |
| 8,885,912 B2 * | 11/2014 | Sui | G06F 19/24 382/128 |
| 9,060,711 B2 * | 6/2015 | Narasimha-Iyer | A61B 3/102 |

(Continued)

FOREIGN PATENT DOCUMENTS

| | | |
|---|---|---|
| WO | 2008/157406 A1 | 12/2008 |
| WO | 2010/134278 A1 | 11/2010 |

(Continued)

OTHER PUBLICATIONS

Wang, Z. (2008). Multiwavelength reflectance confocal microscopy for immune cell identification (Doctoral dissertation, University of Rochester).*

(Continued)

*Primary Examiner* — Vu Le
*Assistant Examiner* — Samah Beg

(57) ABSTRACT

Methods and systems for determining a percentage composition of aqueous cells in an anterior chamber of an eye of a subject based on cell reflectance distributions calculated from OCT image data are disclosed. In one example approach, determining a percentage composition of detected aqueous cells may comprise calculating a percentage of the detected aqueous cells which are polymorphonuclear and calculating a percentage of detected aqueous cells which are mononuclear.

8 Claims, 7 Drawing Sheets

(56) References Cited

U.S. PATENT DOCUMENTS

| | | | |
|---|---|---|---|
| 2004/0189977 A1* | 9/2004 | Nagai | G01N 15/1459 356/39 |
| 2005/0254110 A1* | 11/2005 | Inagaki | G02B 26/125 359/214.1 |
| 2005/0272026 A1* | 12/2005 | Oguni | G01N 33/5094 435/4 |
| 2007/0298454 A1* | 12/2007 | Green | G01N 15/1475 435/34 |
| 2009/0244485 A1* | 10/2009 | Walsh | A61B 3/1005 351/221 |
| 2012/0075638 A1* | 3/2012 | Rollins | A61B 1/00009 356/479 |
| 2013/0071004 A1* | 3/2013 | Yonezawa | G06K 9/0061 382/133 |
| 2013/0100404 A1* | 4/2013 | Narasimha-Iyer | A61B 3/102 351/206 |
| 2013/0149734 A1* | 6/2013 | Ammar | G01N 21/6408 435/29 |
| 2013/0222790 A1* | 8/2013 | Hirao | G01B 9/02061 356/51 |
| 2014/0315237 A1* | 10/2014 | Masujima | G01N 33/48 435/29 |
| 2015/0201829 A1* | 7/2015 | Yang | G01N 21/4795 382/131 |
| 2015/0305614 A1* | 10/2015 | Narasimha-Iyer | G06T 7/0012 351/206 |

FOREIGN PATENT DOCUMENTS

| | | |
|---|---|---|
| WO | 2012/012646 A1 | 1/2012 |
| WO | 2013/097885 A1 | 7/2013 |

OTHER PUBLICATIONS

Houwen, B. (2001). The differential cell count. Laboratory Hematology, 7, 89-100.*

Agrawal, A. (2015). Quantitative Assessment of Optical Coherence Tomography Imaging Performance with Phantom-Based Test Methods and Computational Modeling.*

Agarwal, A., Ashokkumar, D., Jacob, S., Agarwal, A., & Saravanan, Y. (2009). High-speed optical coherence tomography for imaging anterior chamber inflammatory reaction in uveitis: clinical correlation and grading.American journal of ophthalmology, 147(3), 413-416.*

International Appln. No. PCT/US2015/029178, Int. Search Report and Written Opinion, dated Nov. 8, 2016.

Trusko B, et al, "The Standardization of Uveitis Nomenclature (SUN) Project," Methods of Information in Medicine (2013), v52, pp. 259-265.

Jabs Da, et al, Standardization of Uveitis Nomenclature for Reporting Clinical Data. Results of the First International Workshop, American Journal of Ophthalmology (2005), v140, pp. 509-516.

Agarwal A, et al, "High-speed Optical Coherence Tomography for Imaging Anterior Chamber Inflammatory Reaction in Uveitis: Clinical Correlation and Grading," American Journal of Ophthalmology (2009) v147, pp. 413-416.

Li Y, et al, "Anterior Chamber Cell Grading by Optical Coherence Tomography," Investigative Ophthalmology and Visual Science (2013), v54, pp. 258-265.

Li Y, et al, "Aqueous Cell Differentiation in Anterior Uveitis Using Fourier domain Optical Coherence Tomography," ARVO Conference Abstract, Orlando, FL, May 7, 2014, Program No. 4871 Poster Board No. B0247.

* cited by examiner

AQUEOUS CELL DIFFERENTIATION IN ANTERIOR UVEITIS USING OPTICAL COHERENCE TOMOGRAPHY

ACKNOWLEDGMENT OF GOVERNMENT SUPPORT

This invention was made with United States government support under the terms of Grant No. EY018184 awarded by The National Institutes of Health. The United States government has certain rights to the technology.

FIELD

The present disclosure relates to the field of diagnosis of ocular inflammatory conditions, and, more specifically, to methods for diagnosing anterior uveitis using optical coherence tomography.

BACKGROUND

The differential diagnosis of patients presenting ocular inflammatory conditions, such as anterior uveitis, is broad and includes infectious etiologies, systemic autoimmune disease, and malignancy. Currently, treatment is guided by clinical characteristics of the uveitis using the Standardization of Uveitis Nomenclature (SUN) criteria, as described in Trusko B, et al, *Methods of Information in Medicine* 52, 259-265, S251-256 (2013); and Jabs D A et al, *Am J Ophthalmol* 140, 509-516 (2005); both of which are hereby incorporated by reference in their entirety. However, such clinical approaches are subjective and fail to provide information which clarifies the pathogenesis of ocular inflammatory conditions.

Optical coherence tomography (OCT) is a high-resolution, non-contact imaging technology which may be used for imaging cells. Its potential in grading anterior chamber inflammation has been investigated (for example, see Agarwal A et al, *Am J Ophthalmol* 147, 413-416 e4132009; and Li Y et al, *Inv Ophthalmol Vis Sci* 54, 258-265, (2013) both of which are hereby incorporated by reference in their entirety). However, such approaches fail to discern information about cell composition of aqueous cells within the anterior chamber and thus may not be effective in targeting therapy.

SUMMARY

White blood cell (leukocyte) subtypes present in the aqueous humor can be used to clarify pathogenesis of ocular inflammatory conditions, such as anterior uveitis, and can help to target therapy. Current approaches for determining the composition of aqueous cells within the anterior chamber involve diagnostic aqueous taps which are invasive procedures with risks of sight threatening complications such as endophthalmitis.

The present disclosure involves systems and methods that can be used to determine a percentage composition of aqueous cells in an anterior chamber of an eye of a subject based on cell reflectance distributions calculated from OCT image data. In one example approach, the determination of a percentage composition of aqueous cells can comprise calculating a percentage of the detected aqueous cells that are polymorphonuclear and calculating a percentage of detected aqueous cells that are mononuclear.

Such an approach provides a non-invasive method to determine the composition of aqueous inflammatory cells in patients with inflammatory eye diseases such as anterior uveitis, without a diagnostic aqueous tap. Further since OCT ocular imaging has found widespread clinical use and can be performed quickly and easily with minimal expertise, such an approach provides rapid, objective, and reliable diagnosis tools for determining leukocyte subtypes present in the aqueous humor to potentially clarify pathogenesis of ocular inflammatory conditions and help to target therapy.

The methods disclosed herein involve detecting a set of aqueous cells in the anterior chamber of the eye in an OCT image, computing a cell reflectance distribution of the set of aqueous cells, and identifying the cell type of at least one of the cells in the set based upon the cell reflectance distribution. Cell reflectance distribution can be calculated by, for example, calculating a cell reflectance value for each aqueous cell in the set and binning the aqueous cell reflectance values. A cell reflectance value can be calculated as one or more of a peak reflectance, an axial reflectance sum, an area reflectance sum, an axial reflectance average, and an area reflectance average of the set of aqueous cells. An aqueous cell reflectance value can be normalized by, for example, the reflectivity of the reference mirror. The methods can further comprise performing an optimization to fit a cell reflectance distribution to a predetermined polymorphonuclear cell reflectance distribution and a predetermined mononuclear cell reflectance distribution. The polymorphonuclear and mononuclear cell reflectance distribution can be obtained from in vitro measurements. The methods further involve identifying a predominant aqueous cell type in the anterior chamber by calculating the percentage composition of the aqueous cells in the set. The OCT image can be any OCT image including a Fourier domain OCT image.

The methods disclosed herein also involve identifying polymorphonuclear and mononuclear cells in the anterior chamber of the eye by acquiring an OCT image of the anterior chamber of the eye, detecting aqueous cells in the OCT image, calculating an aqueous cell reflectance value for each detected aqueous cell, and binning the calculated aqueous cell reflectance values to generate a cell reflectance distribution of the detected aqueous cells of the OCT image.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
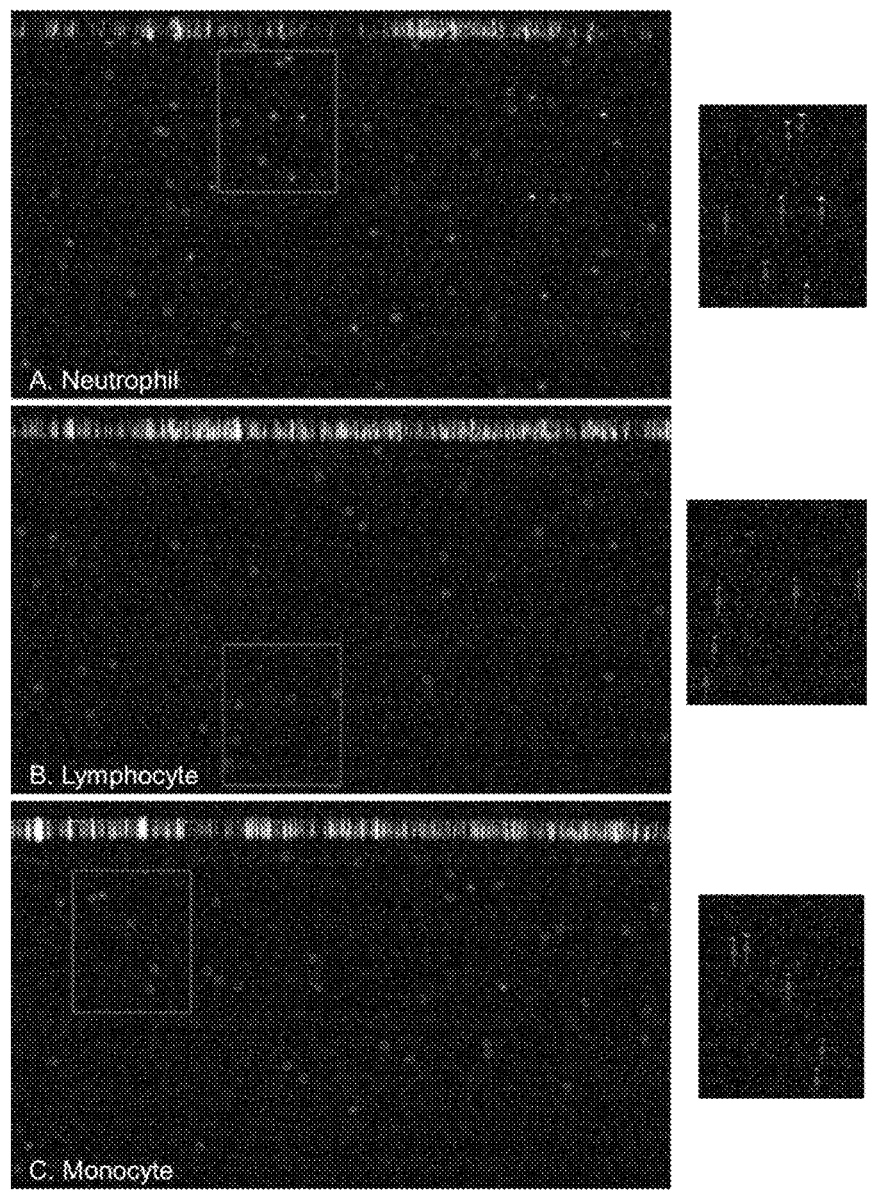
FIG. 1 shows example OCT images with detected aqueous cells.

The following detailed description is directed to systems and methods for determining a percentage composition of aqueous cells in an anterior chamber of an eye of a subject. Cells are identified using cell reflectance distributions calculated from OCT image data. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents. Various operations may be described as multiple discrete operations in turn, in a manner that may be helpful in understanding embodiments; however, the order of description should not be construed to imply that these operations are order dependent.

As remarked above, the differential diagnosis of patients presenting with ocular inflammatory conditions, including anterior uveitis, is broad and can present a diagnostic challenge. The inventors herein have recognized that knowledge of leukocyte subtypes present in the aqueous humor enables improved diagnosis of ocular inflammatory conditions and help to target therapy and/or monitor treatment. Current approaches for determining the composition of aqueous cells within the anterior chamber utilize diagnostic aqueous taps which are invasive procedures with risks of sight threatening complications such as endophthalmitis.

OCT is an optical signal acquisition and processing method that is capable of capturing three-dimensional images at micrometer-resolution from optical scattering media, such as biological tissue. OCT is based on interferometric techniques and typically employs near-infrared light. The use of relatively long wavelength light allows it to penetrate into the scattering medium. OCT-based ocular imaging has found widespread clinical use and can be performed quickly and easily with minimal expertise. OCT is a non-invasive imaging modality which provides accurate and precise anatomical measurements regions of the eye.

Disclosed herein are methods and systems that involve the use of an OCT system to identify and calculate a percentage composition of aqueous cells in an anterior chamber of an eye of a subject based on cell reflectance distributions resulting from OCT image data. For example, aqueous polymorphonuclear cells can be detected and their percentage calculated and aqueous mononuclear cells can be detected and their percentage calculated.

As used herein the term 'aqueous cells' refers to any blood cell type in the aqueous humor of an anterior chamber of an eye. These include white blood cell (leukocyte) types. Examples of aqueous cells include polymorphonuclear and mononuclear cells. As used herein, 'polymorphonuclear' refers to any suitable white blood cell characterized by the presence of granules in the cytoplasm. Polymorphonuclear leukocytes include neutrophils, basophils, and eosinophils. As used herein, 'mononuclear' refers to any suitable white blood cell characterized by the absence of granules in its cytoplasm. Mononuclear leukocytes include B and T lymphocytes as well as monocytes and macrophages.

As used herein, the term 'cell reflectance' refers to any parameter obtained from an OCT image that can be used to identify an individual aqueous cell as belonging to a particular cell type. For example, cell reflectance can refer to an intensity peak (peak reflectance) calculated from the OCT image as a maximum signal intensity of a detected aqueous cell normalized by a maximum signal intensity of a reference mirror. As another example, cell reflectance may refer to an axial intensity sum (axial reflectance sum) calculated from the OCT image as a sum of aqueous cell signal intensities along a depth direction in the OCT image and normalized by a reflectivity of a reference mirror. In other examples, cell reflectance may refer to an axial reflectance average, an area reflectance sum, and/or an area reflectance average of cells identified in the OCT image.

EXAMPLE

The following example illustrates a method, e.g., method 600 described below, for determining a composition of aqueous cells in an anterior chamber of an eye of a subject based on cell reflectance distributions calculated from OCT image data. Such a method may be performed via an OCT system and/or other suitable computing system including processors having physical circuitry programmed to perform one or more of the illustrated steps. It should be understood that this example is for illustrative purposes and is not intended to be limiting.

In this example, different human blood cell types including lymphocytes, neutrophils, monocytes, and red blood cells were characterized using Fourier-domain optical coherence tomography (RTVue-CAM OCT). However, it should be understood that other types of OCT data acquisition protocols may be used without departing from the scope. This example illustrates how OCT data may be used to identify which cell types are present in a patient in order to aid in the diagnosis and treatment of ocular inflammatory conditions, e.g., uveitis. Such an approach may provide a more objective measure of treatment response than the more subjective current grading system described above.

In this example, blood was drawn from healthy volunteers and leukocytes were separated from the blood samples and sorted using standardized methods for cell sorting with an FASC Aria flow cytometer. Three different validated and titered antibodies were used as cell markers: CD45-Pacific orange for lymphocytes, CD14-APC H7 for monocytes, and CD33-Percp Cy5.5 for neutrophils. The FASC Aria flow cytometer was used for cell sorting and 2,088,531 lymphocytes, 1,240,493 monocytes, 4,104,408 neutrophils were isolated from the peripheral blood sample. Approximately 1,000,000 cells of each type were placed in suspension and scanned with a 26 kHz Fourier-domain OCT system (RT-Vue, Optovue, Inc.) with 5 µm axial resolution. Cell suspensions of neutrophils, lymphocytes and monocytes were placed into test tubes and imaged with OCT. A sample of each was also plated on a slide for histological evaluation. For example, FIG. 1 shows example OCT images of different types of aqueous cells in suspension in test tubes. In particular, FIG. 1 shows OCT images of A) neutrophil, B) lymphocyte, and C) monocyte suspensions in test tubes. The cells in each of the OCT images shown in FIG. 1 were detected and identified by customized software. In FIG. 1, the detected aqueous cells are shown marked with circles in the large panels and labeled with arrows in the corresponding magnified panels flanking the large panels. The bright bands shown in the large panels in FIG. 1 were due to artifacts from the test tube wall.

In this example, a clinical study was also performed to image the anterior chamber (AC) of anterior uveitis patients with active inflammation using OCT. Nineteen eyes of 14 anterior uveitis patients were included in the study. As described in more detail below, aqueous cells were detected and measured in the OCT images using automated software. The percentage composition of the aqueous cells was estimated by fitting the axial intensity sum distribution to a linear combination of neutrophil and lymphocyte (as representative of mononuclear cells) distributions. The percentage composition of the aqueous cells was estimated by fitting its cell reflectance distribution to a linear combination of polymorphonuclear (represented by neutrophils) and mononuclear (represented by lymphocytes) cell reflectance distributions. The predominant anterior chamber cell type was identified as the cell type with a percentage composition greater than 50%.

In this example, a 26,000 Hz Fourier-domain OCT system (RTVue, Optovue, Inc., Fremont, Calif., USA) with 5 μm axial resolution was used to image cells both in vitro and in vivo. In particular, cell suspensions of neutrophils, lymphocytes, and monocytes were placed into test tubes and were scanned 3 times with the OCT system. However, it should be understood that any suitable OCT scanning protocol may be used without departing from the scope.

Custom designed software algorithms, examples of which were described above and below with reference to FIG. 6, were used to automatically identify cells as hyper-reflective spots from the OCT images (e.g., see FIG. 1). The average axial width, peak intensity, and axial intensity sum of each cell type was calculated. Axial width was calculated by taking the full-width-half-maximum points on OCT signal intensity profiles. Peak intensity was calculated as the maximum signal intensity of identified cells. The axial intensity sum was calculated as the sum of the cell signal intensity along the depth (z) direction in the OCT image. Both peak intensity and axial intensity sum measurements were normalized by the reflectivity of a reference mirror (reflectivity=1.0). Signal and image processing were performed with MATLAB software version 7.10.0 (Math Works, Inc., Natick, Mass., USA). It was assumed that the axial width, peak intensity, and axial intensity sum measurements were not normally distributed (P<0.001, Kolmogorov-Smirnov test), therefore the omnibus non-parametric Kruskal-Wallis test was performed with pairwise comparisons performed with the Mann-Whitney test for each of the cell types. All analyses used a two-sided alpha of 0.05 to define significance.

Histologic examination confirmed relatively pure samples of each cell population. On static OCT images the cells appeared as hyper-reflective spots which could be identified by the custom computerized algorithm described herein. The cell types could be distinguished from each other by their peak intensity and axial intensity sum as measured on the OCT images. The mean differences in peak intensity were statistically significant between neutrophils, lymphocytes, and red blood cells and each of the other cell types (p<0.001, Kruskal-Wallis). Table 1 shown below displays the average measurements of each of the cell types and their standard deviations for in vitro reflectance measurements by OCT.

TABLE 1

| Cell Type | Axial width (μm) | Intensity peak ($10^{-7}$ reflectivity) | Axial intensity sum ($10^{-7}$ reflectivity × μm) |
| --- | --- | --- | --- |
| Neutrophil | 6.3 ± 1.1 | 2.39 ± 4.38 | 16.93 ± 29.72 |
| Lymphocyte | 6.2 ± 1.1 | 0.81 ± 0.96 | 5.98 ± 5.66 |
| Monocyte | 6.3 ± 1.2 | 0.96 ± 1.10 | 7.07 ± 7.65 |

TABLE 1-continued

| Cell Type | Axial width (μm) | Intensity peak ($10^{-7}$ reflectivity) | Axial intensity sum ($10^{-7}$ reflectivity × μm) |
| --- | --- | --- | --- |
| Red blood cell | 6.4 ± 1.5 | 1.04 ± 1.29 | 7.42 ± 8.37 |

As shown in Table 1, polymorphonuclear cells (neutrophils) had approximately the same apparent size as mononuclear cells (lymphocytes or monocytes), but were significantly brighter in OCT images. As remarked above, any suitable OCT intensity calculation associated with a cell may be used as the cell reflectance for that cell in the calculations described herein. For example, one or more of the intensity peak (peak reflectance), the axial intensity sum (an axial reflectance sum), an area reflectance sum, an axial reflectance average, and an area reflectance average of cells identified in OCT image may be used as a cell reflectance value in the calculations described herein.

Figure 2:
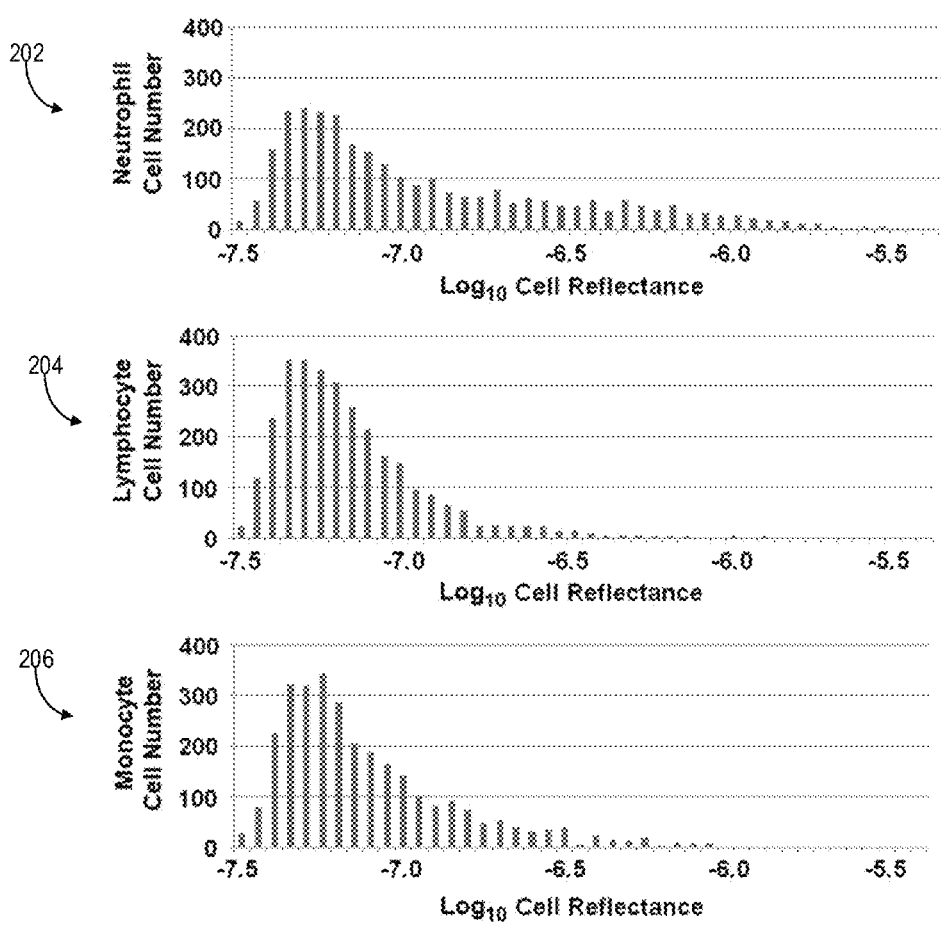
FIG. 2 shows example cell reflectance distributions for different example aqueous cell types.

FIG. 2 shows example cell reflectance distributions (histograms) plotted on a logarithmic scale along the x-axis for different example aqueous cell types. In FIG. 2, cell reflectance corresponds to the intensity peak value for each detected cell and the distribution was formed by binning all the cell reflectance values for the detected cells in the OCT image. In particular, graph 202 in FIG. 2 shows a neutrophil cell reflectance distribution; graph 204, shows a lymphocyte cell reflectance distribution; and graph 206 shows a monocyte cell reflectance distribution. The most striking differences were seen in the neutrophil intensity distributions as compared with the lymphocyte and monocyte distributions.

The Mann-Whitney test was used to compare the average measurements between cell types. No statically significant difference was found between axial width of all 4 cell types (p>0.2). Average intensity peak and axial intensity sum measurements were significantly different between cell types (p<0.0001).

Table 2 shown below demonstrates that the axial width measurements obtained by OCT correspond to nuclear size measurements in suspension. In particular, Table 2 shows a comparison of white blood cells sizes measured in suspension compared with OCT size measurements.

TABLE 2

| | Cell size (μm) | Cell Morphology | Nuclear size (μm) | Nuclear Morphology | Axial width (μm) |
| --- | --- | --- | --- | --- | --- |
| Neutrophil | 8.9 | Ellipse, round or ovoid | 4.35 | Lobulated, 3-5 lobes | 6.3 |
| Lymphocyte | 7.33 | Ellipse, round or ovoid | 6.2 | Round or irregular | 6.2 |
| Monocyte | 9.87 | Round | 6.44 | Kidney shaped or round, eccentric | 6.3 |

No statistically significant differences were found between the axial width of the four cell types (P=0.28, Kruskal-Wallis). However, red blood cells could be distinguished from neutrophils (P=0.02, Two-way Kolmogorov-Smirnov) and lymphocytes (P<0.001, Two-way Kolmogorov-Smirnov) by comparing their axial width distributions. Red blood cells could not be distinguished from monocytes based on their axial width (P=0.29, Mann-Whitney; P=0.18, Two-way Komogorov-Smirnov).

White and red blood cells were isolated from peripheral blood and characterized using a 26,000 Hz Fourier-domain OCT system (RTVue, Optovue, Inc.) with 5 µm axial resolution. Cells in suspension appeared as hyper-reflective spots on OCT and were characterized by their axial width as well as their signal intensity, including peak intensity and axial intensity sum. Statistical differences in mean signal intensity measurements between neutrophils and lymphocytes, monocytes or erythrocytes were shown which can be used to identify groups of cells. It was hypothesized that peak intensity and axial width measurements are derived from the cell nucleus, except in the case of red blood cells, which do not have nuclei. In this case, the whole cell is approximately the same size as the other cell nuclei, and (without being bound by theory) that OCT is detecting hemoglobin in the cytoplasm.

This example demonstrates the ability of OCT to distinguish neutrophils from the other cell types. In particular, this example demonstrates the ability of OCT to differentiate between polymorphonuclear leukocytes (e.g., neutrophils, basophils, and eosinophils) which have a higher reflectance distribution due to their segmented nuclear shape, from mononuclear leukocytes (e.g., lymphocytes) which have lower reflectance distributions due to their round nuclear shape.

Figure 3:
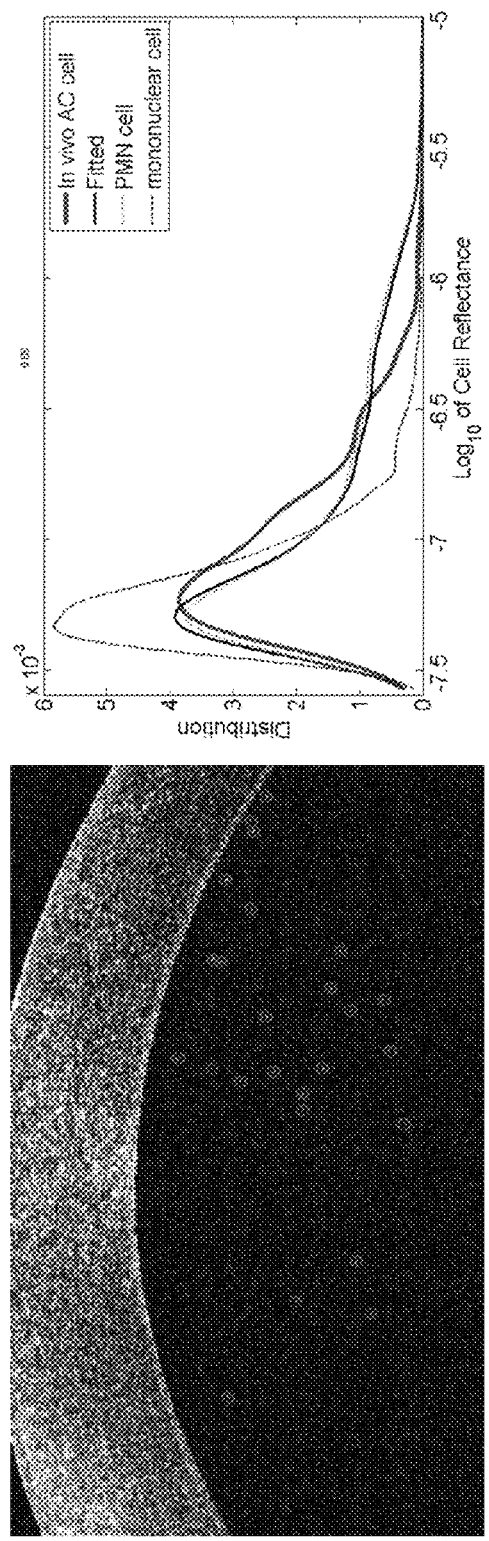
FIGS. 3-5 show example OCT images of an anterior chamber of an eye and corresponding cell reflectance distributions used to determine aqueous cell compositions in the anterior chamber.
Figure 4:
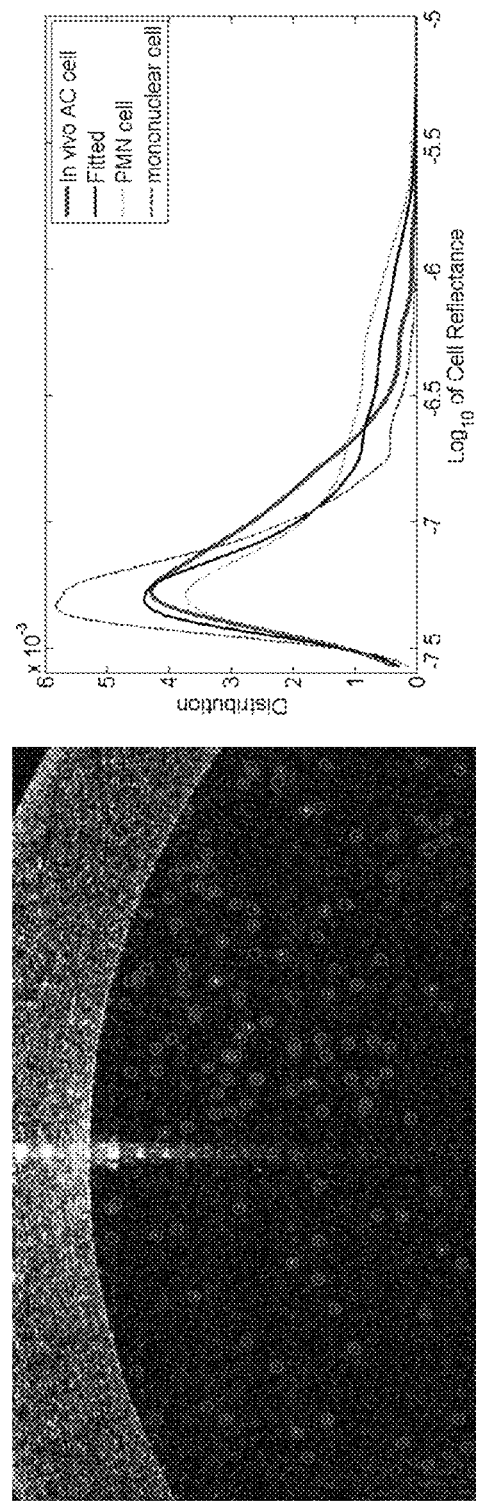
Figure 5:
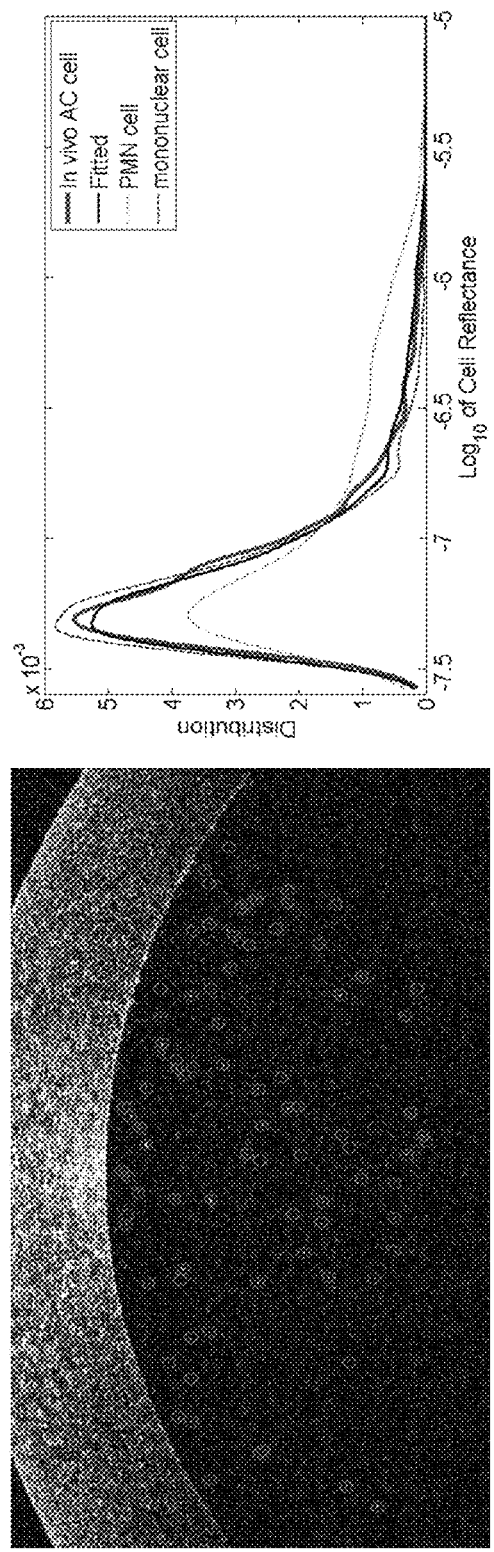

For example, FIGS. 3-5 shows example OCT images of an anterior chamber of an eye and corresponding cell reflectance distributions used to determine aqueous cell compositions in the anterior chamber. The left panels in FIGS. 3-5 show OCT images of an anterior chamber with detected aqueous cells marked with circles. The right panels in FIGS. 3-5 show the aqueous cell reflectance distribution obtained from the OCT image overlaid onto a predetermined polymorphonuclear (PMN) cell reflectance distribution and a predetermined mononuclear cell distribution. The right panels in FIGS. 3-5 also show a fitted distribution obtained by fitting a linear combination of the predetermined polymorphonuclear cell reflectance distribution and the predetermined mononuclear cell distribution to the aqueous cell reflectance distribution. As described in more detail below, this fitting may be used to determine a percentage composition of polymorphonuclear and mononuclear cells in the anterior chamber which may, in turn, be used to determine a predominate cell type in the anterior chamber.

In particular, FIG. 3 shows data obtained from the left eye of an HLA-B27 positive patient with sudden onset of scleritis. In this example, the OCT anterior chamber cell reflectance distribution was fit with 98% polymorphonuclear cells and 2% mononuclear cells. FIG. 4 shows data obtained from the right eye of an HLA-B27 positive acute anterior uveitis case with sudden onset. In this example, the OCT anterior chamber cell reflectance distribution was fit with a composition of 72% polymorphonuclear cells and 28% mononuclear cells. FIG. 5 shows data obtained from the left eye of a patient with Crohn's disease, recent flare-up. In this example, the OCT anterior chamber cell reflectance distribution was fit with 16% polymorphonuclear cells and 84% mononuclear; thus, mononuclear cells were identified as the dominant cell type in this example.

Figure 6:
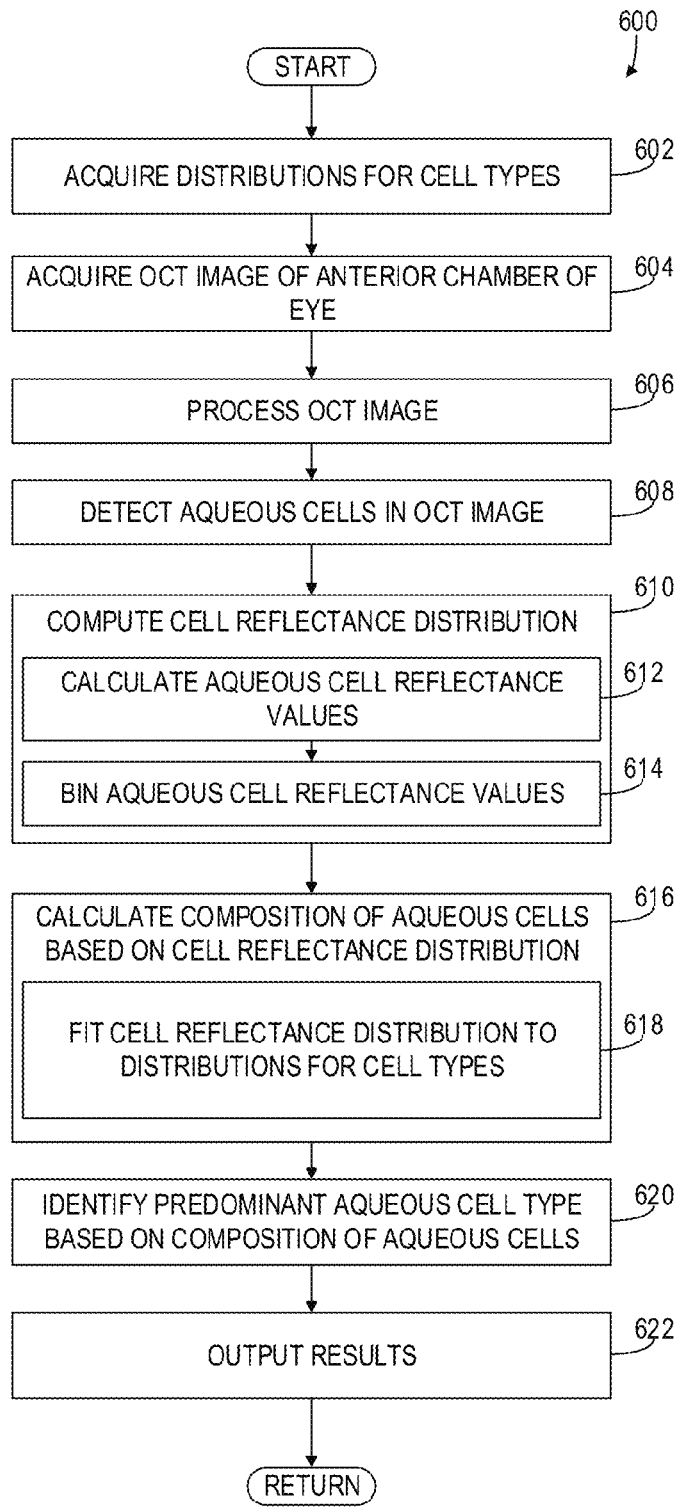
FIG. 6 shows an example method for determining a composition of aqueous cells in an anterior chamber of an eye using OCT imaging in accordance with the disclosure.

FIG. 6 shows an example method 600 for determining a composition of aqueous cells in an anterior chamber of an eye of a subject based on cell reflectance calculated from an OCT image. For example, the aqueous cells may comprise aqueous inflammatory cells and method 600 may be used to determining a percentage composition of polymorphonuclear cells and mononuclear cells in the anterior chamber.

One or more steps of method 600 may be performed by one or more computing devices, such as the computing device described below with regard to FIG. 7. Examples of such computing devices include an OCT image acquisition system, one or more processors included in an OCT system, one or more image processors, and/or any other suitable processors which include physical circuitry programmed to automatically perform various acts of method 600. It should be understood that the various acts illustrated in method 600 may be performed in the sequence illustrated, in other sequences, in parallel, or in some cases omitted. Further, in some examples method 600 may be repeated in order to determine the composition of aqueous cells in the anterior chambers of multiple eyes.

At 602, method 600 includes acquiring distributions for cell types. For example, a predetermined polymorphonuclear cell reflectance distribution and a predetermined mononuclear cell reflectance distribution may be obtained from in vitro polymorphonuclear and mononuclear cell reflectance measurements, respectively. These predetermined call reflectance distributions may comprise probability distributions and may be estimated, measured, or calculated in any suitable way. In some examples, the predetermined call reflectance distributions may be stored in a memory component of a computing device and used during a fitting procedure performed by a processor to calculate cell compositions from OCT image data as described below.

At 604, method 600 includes acquiring an OCT image of an anterior chamber of an eye of a subject. For example, an OCT system may be utilized to acquire one or more OCT images of the anterior chamber using any suitable OCT imaging protocol. As another example, the OCT data may be received by a computing device from an OCT scanning system via a network or from storage medium coupled to the computing device. The OCT data may be obtained from any suitable OCT scanning device, e.g., a swept-source Fourier-domain OCT scanner, a time-domain OCT scanner, or any other suitable OCT scanning technology.

At 606, method 600 may include processing the OCT image data. Various processing algorithms may be applied to the OCT data in order to condition the image data for detection of aqueous cells in the image and extraction of intensity or reflectance parameters. For example, the OCT image may be filtered, motion reduced, normalized, etc.

At 608, method 600 includes detecting aqueous cells in the OCT image. Aqueous cells may be automatically detected in the OCT image in any suitable way. For example, an image processor may be utilized to identify cells as hyper-reflective spots from the OCT images as illustrated in FIG. 1 described above.

At 610, method 600 includes computing a cell reflectance distribution of the detected aqueous cells in the OCT image. Computing a cell reflectance distribution of the detected aqueous cells may include, for each detected cell, calculating an average axial width, peak intensity, and axial intensity sum. For example, the axial width may be calculated by computing the full-width-half-maximum points on OCT signal intensity profiles. Peak intensity may be calculated as a maximum signal intensity of identified cells. The axial intensity sum may be calculated as the sum of the cell signal intensity along the depth (z) direction in the OCT image. In some examples, both peak intensity and axial intensity sum measurements may be normalized by the reflectivity of a reference mirror (reflectivity=1.0).

In particular, at 612, method 600 may include calculating an aqueous cell reflectance value for each detected cell in the OCT image. For example, for each detected cell, the aqueous cell reflectance value may be calculated from the OCT image as a maximum signal intensity of the detected cell normalized by a maximum signal intensity of a reference mirror. As another example, for each detected cell, the aqueous cell reflectance value may be calculated from the OCT image as a sum of aqueous cell signal intensities along a depth direction in the OCT image and normalized by a reflectivity of a reference mirror. In other examples, calculating an aqueous cell reflectance value may include calculating one or more of a peak reflectance, an axial reflectance sum, an area reflectance sum, an axial reflectance average, and an area reflectance average of cells identified in OCT image.

In order to calculate the cell reflectance distribution, at 614, method 600 includes binning the calculated reflectance values to generate a cell reflectance probability distribution ($P_{eye}$) of the detected aqueous cells in the OCT image. In some examples, a plurality of different cell reflectance distributions may be calculated from the OCT image. For example, a plurality of cell reflectance distributions may be computed by binning one or more of the peak reflectance values, the axial reflectance sums, the area reflectance sums, the axial reflectance averages, and the area reflectance averages of cells identified in OCT image.

At 616, method 600 includes calculating a percentage composition of the detected aqueous cells based on the cell reflectance distributions. Calculating a percentage composition of the detected aqueous cells may be performed in any suitable way and may be based on one or more cell reflectance distributions calculated from the OCT image. For example, a percentage composition may be obtained by performing a suitable optimization process to fit one or more of a peak reflectance distribution, an axial reflectance sum distribution, an area reflectance sum distribution, an axial reflectance average distribution, and an area reflectance average of cells distribution to predetermined distributions for different cell types, e.g., a predetermined distribution for polymorphonuclear cell types and a predetermined distribution for mononuclear cell types.

For example, at 618, method 600 may include fitting the cell reflectance distribution to a linear combination of a predetermined polymorphonuclear cell reflectance distribution and a predetermined mononuclear cell reflectance distribution. In some examples, the predetermined polymorphonuclear cell reflectance distribution and the predetermined mononuclear cell reflectance distribution may be obtained from in vitro polymorphonuclear and mononuclear cell reflectance measurements. The cell reflectance distribution may be fit to a linear combination, or any other suitable function, of any number of different cell type distributions. The coefficients generated from the fitting provide estimates of the relative compositions of the different cell types in the OCT image.

As an example, fitting the cell reflectance distribution to a linear combination of a predetermined polymorphonuclear cell reflectance distribution and a predetermined mononuclear cell reflectance distribution may comprise calculating a fitted cell reflectance probability distribution, $P_{fitted}$, by minimizing an objective function value to optimize t % using the following Equation 1:

$$P_{fitted} = (100\% - t\%) \times P_{PMN} + t\% \times P_{Mono} \quad \text{(Eq. 1)}$$

In Equation 1, t % is a percentage of mononuclear cells in the anterior chamber, (100%-t %) is a percentage of polymorphonuclear cells in the anterior chamber, $P_{PMN}$ is the predetermined polymorphonuclear cell reflectance distribution, and $P_{Mono}$ is the predetermined mononuclear cell reflectance distribution. Any suitable objective function value may be used, e.g., the objective function value may be defined by a root-mean-square difference between the cell reflectance distribution and $P_{fitted}$.

At 620, method 600 may include identifying a predominant aqueous cell type in the anterior chamber based on the computed percentage composition of the detected aqueous cells. For example, an aqueous cell type may be identified as predominant in response to the calculated percentage composition of that aqueous cell type being greater than approximately 50%. In this way, by taking the average measurements of cells within the anterior chamber it may be possible to calculate the probability that the cells as a group represent predominantly neutrophils versus lymphocytes or monocytes, for example.

At 622, method 600 may include outputting results. For example, the calculated percentage compositions and/or the identified predominant cell type may be provided as any suitable output via a computing device. For example, a visual indication or data may be output to a display device coupled to the computing device, an audio indication may be output to one or more speakers coupled to the computing device, and/or data may be stored in a storage medium of the computing device and/or output to an external device via a network.

In some embodiments, the above described methods and processes may be tied to a computing system, including one or more computers. In particular, the methods and processes described herein, e.g., method 600 described above, may be implemented as a computer application, computer service, computer API, computer library, and/or other computer program product.

Figure 7:
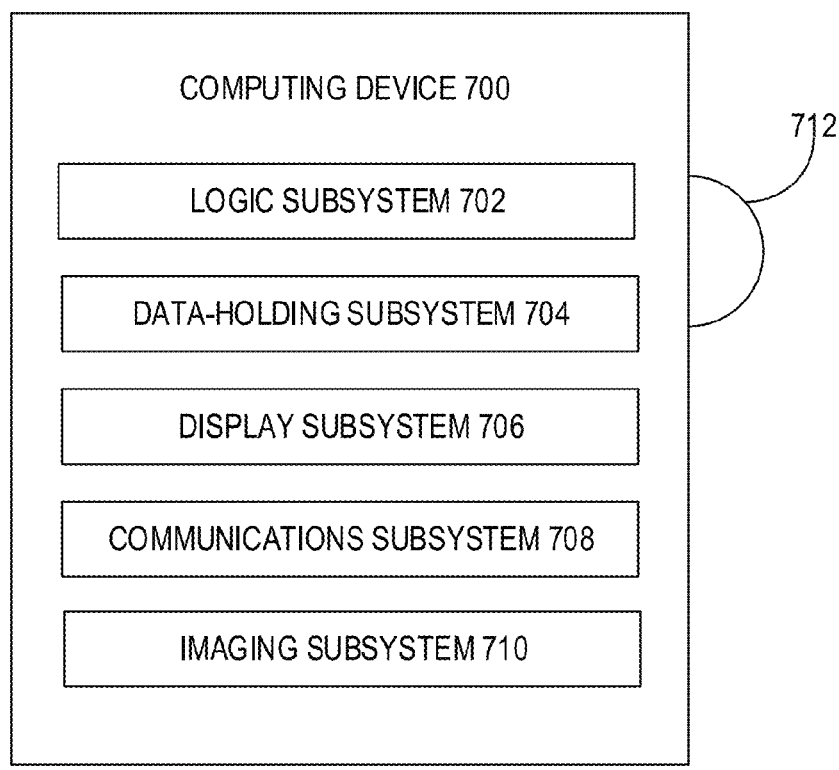
FIG. 7 schematically shows an example computing system in accordance with the disclosure.

FIG. 7 schematically shows a non-limiting computing device 700 that may perform one or more of the above described methods and processes. For example, FIG. 7 may represent an OCT data acquisition system, an image processing system, and/or any suitable processor which includes circuitry programmed to perform the various operations described herein. Computing device 700 is shown in simplified form. It is to be understood that virtually any computer architecture may be used without departing from the scope of this disclosure. In different embodiments, computing device 700 may take the form of a microcomputer, an integrated computer circuit, microchip, a mainframe computer, server computer, desktop computer, laptop computer, tablet computer, home entertainment computer, network computing device, mobile computing device, mobile communication device, gaming device, etc.

Computing device 700 includes a logic subsystem 702 and a data-holding subsystem 704. Computing device 700 may optionally include a display subsystem 706 and a communication subsystem 708, and/or other components not shown in FIG. 7. Computing device 700 may also optionally include user input devices such as manually actuated buttons, switches, keyboards, mice, game controllers, cameras, microphones, and/or touch screens, for example.

Logic subsystem 702 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 704 may include one or more physical, non-transitory devices configured to hold data and/or instructions executable by the logic subsystem to implement the herein described methods and processes. When such methods and processes are implemented, the state of data-holding subsystem 704 may be transformed (e.g., to hold different data).

Data-holding subsystem 704 may include removable media and/or built-in devices. Data-holding subsystem 704 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 704 may include devices with one or more of the following characteristics: volatile, nonvolatile, dynamic, static, read/write, read-only, random access, sequential access, location addressable, file addressable, and content addressable. In some embodiments, logic subsystem 702 and data-holding subsystem 704 may be integrated into one or more common devices, such as an application specific integrated circuit or a system on a chip.

FIG. 7 also shows an aspect of the data-holding subsystem in the form of removable computer-readable storage media 712, which may be used to store and/or transfer data and/or instructions executable to implement the herein described methods and processes. Removable computer-readable storage media 712 may take the form of CDs, DVDs, HD-DVDs, Blu-Ray Discs, EEPROMs, flash memory cards, and/or floppy disks, among others.

When included, display subsystem 706 may be used to present a visual representation of data held by data-holding subsystem 704. As the herein described methods and processes change the data held by the data-holding subsystem, and thus transform the state of the data-holding subsystem, the state of display subsystem 706 may likewise be transformed to visually represent changes in the underlying data. Display subsystem 706 may include one or more display devices utilizing virtually any type of technology. Such display devices may be combined with logic subsystem 702 and/or data-holding subsystem 704 in a shared enclosure, or such display devices may be peripheral display devices. In some embodiments, computing device 700 may additionally include an audio subsystem including one or more speakers which may be used to present audio representations of data held by data-holding subsystem 704.

When included, imaging subsystem 710 may be used acquire and/or process any suitable image data from various sensors or imaging devices in communication with computing device 700. For example, imaging subsystem 710 may be configured to acquire OCT image data as part of an OCT system. Imaging subsystem 710 may be combined with logic subsystem 702 and/or data-holding subsystem 704 in a shared enclosure, or such imaging subsystems may comprise periphery imaging devices. Data received from the imaging subsystem may be held by data-holding subsystem 704.

When included, communication subsystem 708 may be configured to communicatively couple computing device 700 with one or more other computing devices. Communication subsystem 708 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 700 to send and/or receive messages to and/or from other devices via a network such as the Internet.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computerized method of identifying aqueous cells in an anterior chamber of an eye of a subject, the method comprising:
receiving an optical coherence tomography (OCT) image of the anterior chamber;
detecting a set of aqueous cells in the OCT image;
computing a cell reflectance distribution of the set of aqueous cells by calculating an aqueous cell reflectance value for each aqueous cell in the set and binning the calculated aqueous cell reflectance values;
identifying the cell type of at least of the aqueous cells in the set based on the cell reflectance distribution; and
performing an optimization to fit the cell reflectance distribution to a predetermined polymorphonuclear cell reflectance distribution and a predetermined mononuclear cell reflectance distribution.

2. The method of claim 1, wherein the predetermined polymorphonuclear cell reflectance distribution and the predetermined mononuclear cell reflectance distribution are obtained from in vitro cell reflectance measurements.

3. The method of claim 1, wherein performing an optimization to fit the cell reflectance distribution to a predetermined polymorphonuclear cell reflectance distribution and a predetermined mononuclear cell reflectance distribution comprises calculating a fitted cell reflectance probability distribution, $P_{fitted}$, by minimizing an objective function value to optimize t % using the equation $$P_{fitted} = (100\% - t\%) \times P_{PMN} + t\% \times P_{Mono},$$

where t % is a percentage of mononuclear cells in the anterior chamber, (100%−t %) is a percentage of polymorphonuclear cells in the anterior chamber, $P_{PMN}$ is the predetermined polymorphonuclear cell reflectance distribution, and $P_{Mono}$ is the predetermined mononuclear cell reflectance distribution.

4. The method of claim 3, where the objective function value is defined by a root-mean-square difference between the cell reflectance distribution and $P_{fitted}$.

5. A method for identifying polymorphonuclear cells and mononuclear cells in an anterior chamber of an eye with an optical coherence tomography (OCT) system, the method comprising:
   acquiring an OCT image of the anterior chamber of the eye;
   detecting aqueous cells in the OCT image;
   from the OCT image, calculating an aqueous cell reflectance value for each detected aqueous cell;
   binning the calculated aqueous cell reflectance values to generate a cell reflectance distribution of the detected aqueous cells in the OCT image; and
   calculating a percentage of the detected aqueous cells which are polymorphonuclear and calculating a percentage of the detected aqueous cells which are mononuclear by fitting the cell reflectance distribution to a linear combination of a predetermined polymorphonuclear cell reflectance distribution and a predetermined mononuclear cell reflectance distribution.

6. The method of claim 5, wherein the predetermined polymorphonuclear cell reflectance distribution and the predetermined mononuclear cell reflectance distribution are obtained from in vitro polymorphonuclear and mononuclear cell reflectance measurements.

7. The method of claim 6, wherein fitting the cell reflectance distribution to a linear combination of a predetermined polymorphonuclear cell reflectance distribution and a predetermined mononuclear cell reflectance distribution comprises calculating a fitted cell reflectance probability distribution, $P_{fitted}$, by minimizing an objective function value to optimize t % using the equation $$P_{fitted}=(100\%-t\%)\times P_{PMN}+t\%\times P_{Mono},$$

where t % is a percentage of mononuclear cells in the anterior chamber, (100%–t %) is a percentage of polymorphonuclear cells in the anterior chamber, $P_{PMN}$ is the predetermined polymorphonuclear cell reflectance distribution, and $P_{Mono}$ is the predetermined mononuclear cell reflectance distribution.

8. The method of claim 5, further comprising identifying a predominant aqueous cell type in the anterior chamber based on the calculated percentages.

* * * * *